US007880016B2

(12) United States Patent
Zerban et al.

(10) Patent No.: US 7,880,016 B2
(45) Date of Patent: *Feb. 1, 2011

(54) PROCESS FOR THE PREPARATION OF THE SALTS OF 4-(BENZIMIDAZOLYLMETHYL-AMINO)-BENZAMIDES

(75) Inventors: Georg Zerban, Ingelheim (DE); Arndt Hausherr, Mainz (DE); Kerstin Schlarb, Baerweiler (DE); Rainer Hamm, Ingelheim (DE); Gunter Koch, Schwabenheim (DE); Bjoern Weyell, Aspisheim (DE); Heinz-Peter Schmitt, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/614,299

(22) Filed: Dec. 21, 2006

(65) Prior Publication Data

US 2007/0185173 A1    Aug. 9, 2007

(30) Foreign Application Priority Data

Dec. 21, 2005    (DE)    ........................ 10 2005 061 624

(51) Int. Cl.
*C07D 235/16* (2006.01)
(52) U.S. Cl. .................................................. 548/309.7
(58) Field of Classification Search ............... 548/309.7
See application file for complete search history.

(56) References Cited

U.S. PATENT DOCUMENTS

| 6,087,380 | A | 7/2000 | Hauel et al. | |
|---|---|---|---|---|
| 6,248,770 | B1 | 6/2001 | Ries et al. | |
| 6,451,832 | B2 | 9/2002 | Ries et al. | |
| 7,202,368 | B2 * | 4/2007 | Zerban et al. | ............ 548/304.7 |
| 2007/0149589 | A1 | 6/2007 | Zerban et al. | |

FOREIGN PATENT DOCUMENTS

| CA | 2337804 A1 | 1/2000 |
|---|---|---|
| CA | 2393916 A1 | 9/2008 |
| EP | 1609784 A1 | 12/2005 |
| WO | 2277949 A1 | 8/1998 |
| WO | 2006/000353 A1 | 1/2006 |

OTHER PUBLICATIONS

International Search Report—PCT/EP2006/070034—May 7, 2007.
Anbazhangan, et al., "Direct conversion of amidoximes to amidines via transfer hydrogenation," 2003, p. 2467-2469, No. 16, Synthesis, Department of Chemistry, Georgia State University, Atlanta, GA, USA.
Peterlin-Masic, et al: "Arginine mimetics" 2001, p. 7073-7105, vol. 57, No. 33, Tetrahedron, Elsevier Science Publishers, Amsterdam, NL, Department of Pharmacy, University of Ljubljana, Ljubjana, Slovenia.
Liao, et al: "New selective and potent 5-HT 1B/1D antagonist: chemistry and pharmacological evaluation of N-piperazinylphenyl biphenylcarboxamides and biphenylsufonamides" 2000, p. 517-525, vol. 43,Journal of Medicinal Chemistry, American Chemical Society, Department of Medicinal Chemistry, Center for Pharmacy, University of Groningen, Groningen, The Netherlands, Preclinical Pharmaceutical Research, Merck KGaA, Dartstadt, Germany and Department of Medical Biochemistry, University of Goteborg, Goteborg, Sweden.
Bolton, et al: "3-Substituted-1,2,4-oxadiazolin-5-one; A useful amidine precursor and protecting group" 1995, p. 4471-4474, vol. 36, No. 25, Tetrahedron Letters, Elsevier, Amsterdam NL, Glaxo Research and Development Ltd, Glaxo Medicines Research Centre, Stevenage, UK.

* cited by examiner

*Primary Examiner*—Laura L. Stockton
(74) *Attorney, Agent, or Firm*—Michael P. Morris; Wendy A. Petka

(57) ABSTRACT

The invention relates to a process for preparing a salt of an optionally substituted 4-benzimidazol-2-ylmethylamino)-benzamidine, characterised in that
(a) an optionally correspondingly substituted diaminobenzene is condensed with 2-[4-(1,2,4-oxadiazol-5-on-3-yl)-phenylamino]-acetic acid,
b) i) the product thus obtained is hydrogenated,
  ii) optionally the amidino group is carbonylated, without isolating the intermediate product of the hydrogenation beforehand and
  iii) without prior isolation of the intermediate product of the carbonylation the desired salt is isolated.

9 Claims, No Drawings

PROCESS FOR THE PREPARATION OF THE SALTS OF 4-(BENZIMIDAZOLYLMETHYL-AMINO)-BENZAMIDES

RELATED APPLICATIONS

This application claims priority to German application DE 10 2005 061 624.0 filed Dec. 21, 2005, which is hereby incorporated by reference.

BACKGROUND TO THE INVENTION

1. Technical Field

The invention relates to a process for preparing a salt of an optionally substituted 4-(benzimidazol-2-ylmethylamino)-benzamidine, wherein
(a) an optionally correspondingly substituted diaminobenzene is condensed with 2-[4-(1,2,4-oxadiazol-5-on-3-yl)-phenylamino]-acetic acid and
(b) i) the product thus obtained is hydrogenated,
  ii) optionally the amidino group is carbonylated without isolating the intermediate product of the hydrogenation beforehand.

2. Prior Art

Substituted (4-benzimidazol-2-ylmethylamino)-benzamidines, particularly 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide are already known from International Patent Application WO 98/37075 as active substances with a thrombin-inhibiting and thrombin time prolonging activity.

The main types of indication for the compound of chemical formula I are the postoperative prevention of deep vein thrombosis and the prevention of stroke (prevention of stroke due to atrial fibrillation, SPAF for short).

In WO 98/37075 it is proposed that the substituted (4-benzimidazol-2-ylmethylamino)-benzamidines be prepared by reacting the corresponding substituted (4-benzimidazol-2-ylmethylamino)-benzonitriles with ammonia. This process is highly complex from the point of view of production technology and results in a high loading of acids that have to be disposed of.

The aim of the present invention was to indicate an alternative method of preparing the substituted (4-benzimidazol-2-ylmethylamino)-benzamidines, by which this technologically complex step could be avoided.

BRIEF SUMMARY OF THE INVENTION

Surprisingly it has now been found that the salts of the substituted 4-(benzimidazol-2-ylmethylamino)-benzamidines can be produced in high yields and using inexpensive adjuvants if
(a) an optionally correspondingly substituted diaminobenzene is condensed with 2-[4-(1,2,4-oxadiazol-5-on-3-yl)-phenylamino]-acetic acid and
(b) i) the product thus obtained is hydrogenated,
  ii) optionally the amidino group is carbonylated, without isolating the intermediate product of the hydrogenation beforehand and
  iii) without prior isolation of the intermediate product of the carbonylation the desired salt is isolated.

DETAILED DESCRIPTION OF THE INVENTION

A process for preparing a salt of an optionally substituted 4-(benzimidazol-2-ylmethylamino)-benzamidine of formula (I) with an inorganic or organic acid is preferred

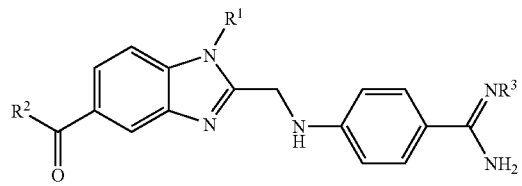

(I)

wherein $R^1$ denotes a $C_{1-6}$-alkyl or $C_{3-7}$-cycloalkyl group, $R^2$ (i) denotes a $C_{1-6}$-alkyl group, a $C_{3-7}$-cycloalkyl group optionally substituted by a $C_{1-3}$-alkyl group, while the $C_{1-3}$-alkyl group may additionally be substituted by a carboxyl group or by a group which may be converted in vivo into a carboxy group, or (ii) denotes an $R^{21}NR^{22}$ group, wherein $R^{21}$ denotes a $C_{1-6}$ alkyl group which may be substituted by a carboxy, $C_{1-6}$ alkoxycarbonyl, benzyloxycarbonyl, $C_{1-3}$-alkylsulphonylaminocarbonyl, phenylsulphonylaminocarbonyl, trifluorosulphonylamino, trifluorosulphonylaminocarbonyl or 1H-tetrazolyl group, a $C_{2-4}$-alkyl group substituted by a hydroxy, phenyl-$C_{1-3}$-alkoxy, carboxy-$C_{1-3}$-alkylamino, $C_{1-3}$-alkoxycarbonyl-$C_{1-3}$-alkylamino, N-($C_{1-3}$-alkyl)-carboxy-$C_{1-3}$-alkylamino or N-($C_{1-3}$-alkyl)-$C_{1-3}$-alkoxycarbonyl-$C_{1-3}$-alkylamino group, while in the above-mentioned groups the carbon atom in the α-position to the adjacent nitrogen atom cannot be substituted, or a piperidinyl group optionally substituted by a $C_{1-3}$-alkyl group, and $R^{22}$ denotes a hydrogen atom, a $C_{1-6}$-alkyl group, a $C_{3-7}$-cycloalkyl group optionally substituted by a $C_{1-3}$-alkyl group, or a $C_{3-6}$-alkenyl or $C_{3-6}$-alkynyl group, while the unsaturated moiety may not be linked directly to the nitrogen atom of the $R^{21}NR^{22}$ group, a phenyl group optionally substituted by a fluorine, chlorine or bromine atom, by a $C_{1-3}$-alkyl or $C_{1-3}$-alkoxy group, or a benzyl, oxazolyl, isoxazolyl, thiazolyl, isothiazolyl, pyrazolyl, pyridinyl, pyrimidinyl, pyrazinyl, pyridazinyl, pyrrolyl, thienyl or imidazolyl group optionally substituted by a $C_{1-3}$-alkyl group, or $R^{21}$ and $R^{22}$ together with the nitrogen atom between them denote a 5- to 7-membered cycloalkyleneimino group optionally substituted by a carboxy or $C_{1-4}$-alkoxycarbonyl group, to which additionally a phenyl ring may be fused, and $R^3$ denotes a hydrogen atom, a $C_{1-9}$-alkoxycarbonyl, cyclohexyloxycarbonyl, phenyl-$C_{1-3}$-alkoxycarbonyl, benzoyl, p-$C_{1-3}$-alkyl-benzoyl or pyridinoyl group, wherein the ethoxy moiety in the 2 position of the above-mentioned $C_{1-9}$-alkoxycarbonyl group may additionally be substituted by a $C_{1-3}$-alkylsulphonyl or 2-($C_{1-3}$-alkoxy)-ethyl group, while in step (a) a phenyldiamine of formula (II)

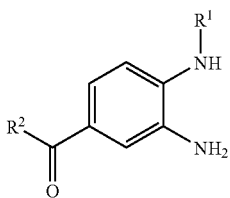

wherein $R^1$ and $R^2$ have the meanings given for formula (I), is reacted with 2-[4-(1,2,4-oxadiazol-5-on-3-yl)-phenylamino]-acetic acid, the resulting product of formula (III)

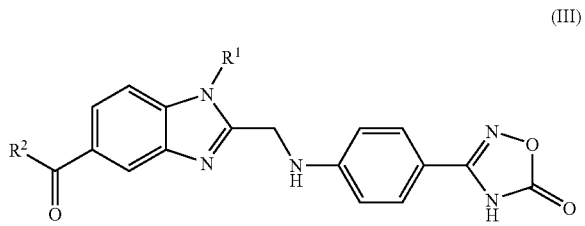

wherein $R^1$ and $R^2$ have the meanings given for formula (I), is hydrogenated in step (b)i), subsequently, without any prior isolation of the hydrogenation product, the compound of formula (I) thus obtained wherein $R^3$ denotes hydrogen is optionally reacted in step (b)ii) with a compound of formula (IV)

wherein $R^3$ has the meaning given for formula (I), and
X denotes a suitable leaving group,
and then without previous isolation of the carbonylation product, in a step (b)iii) the compound of formula (I) thus obtained wherein $R^1$, $R^2$ and $R^3$ are as hereinbefore defined is converted into the desired salt, particularly into a pharmaceutically acceptable salt.

Particularly preferred are the processes according to the invention for preparing the salts of the compounds of formula (I), wherein
$R^1$ denotes a $C_{1-3}$-alkyl group,
$R^2$ denotes an $R^{21}NR^{22}$ group, wherein
  $R^{21}$ denotes a $C_{1-3}$ alkyl group which may be substituted by a carboxy, $C_{1-3}$ alkoxycarbonyl, and
  $R^{22}$ denotes a hydrogen atom, a $C_{1-3}$-alkyl group, a pyridinyl group optionally substituted by a $C_{1-3}$-alkyl group, and
$R^3$ denotes a hydrogen atom, a $C_{1-8}$-alkoxycarbonyl group.

Most preferred are the processes according to the invention for preparing the salts of the compound of formula (I), wherein
$R^1$ denotes a methyl group,
$R^2$ denotes an $R^{21}NR^{22}$ group, wherein
  $R^{21}$ denotes an ethyl group which is substituted by an ethoxycarbonyl group, and
  $R^{22}$ denotes a pyridin-2-yl group, and
$R^3$ denotes an n-hexyloxycarbonyl group.

Preferred salts are the methanesulphonate, chloride, maleate, tartrate, salicylate, citrate and malonate of the compound of formula (I). A particularly preferred salt is the methanesulphonate.

The following embodiments (A) to (F) of the process according to the invention are preferred:

(A) The condensation of step (a) is carried out in the presence of an inert diluent and a water-binding agent.

The correspondingly substituted diaminobenzenes of formula (II) are known e.g. from International Patent Application WO 98/37075, e.g. from Example 25 (Steps a and b), or may be prepared analogously to those described therein. For the hydrogenation of the nitro precursor compound for preparing the diaminobenzene of formula (II) the solvent used may be, for example, toluene, isopropanol, triethylamine, ethanol, butyl acetate, ethyl acetate, methanol or mixtures of these solvents. Preferably, the hydrogenation is carried out under a hydrogen pressure of 1 to 20 bar, but higher pressures are also possible. The concentration of the aromatic nitrogen compound (educt) is conveniently 10 to 40 wt. %; it is more preferably present in a concentration of 20 to 30 wt. %. The catalyst used may be for example 5-10% palladium on charcoal, while preferably 2-20 wt. % of wet charcoal-palladium catalyst is used, based on the aromatic nitrogen compound, which corresponds to about 0.05-1 wt. % palladium based on the aromatic nitrogen compound. Particularly preferably, 3-amino-4-methylaminobenzoic acid amides are used, particularly 3-amino-4-methylaminobenzoic acid-N-(2-pyridyl)-N-(2-ethoxycarbonylethyl)-amide.

The inert diluents used may be both aprotic apolar solvents—such as e.g. aliphatic or aromatic, optionally halogenated hydrocarbons—or aprotic polar solvents such as e.g. ethers and/or amides or lactams and/or mixtures thereof. The aprotic apolar solvents used are preferably branched or unbranched $C_5$-$C_8$ aliphatic alkanes, $C_4$-$C_{10}$ cycloalkanes, $C_1$-$C_6$ aliphatic haloalkanes, $C_6$-$C_{10}$ aromatic alkanes or mixtures thereof. It is particularly preferable to use alkanes such as pentane, hexane or heptane, cycloalkanes such as cyclohexane or methylcyclohexane, haloalkanes such as dichloromethane, aromatic alkanes such as benzene, toluene or xylene or mixtures thereof Suitable aprotic solvents are polar ethers such as, for example, tetrahydrofuran (THF), methyltetrahydrofuran, dioxane, tert-butyl-methylether or dimethoxyethylether or amides such as, for example, dimethylformamide, or lactams such as N-methylpyrrolidone, for example.

Water-binding agents which may be used are hygroscopic salts, inorganic or organic acids or the acid chlorides thereof, anhydrides of inorganic or organic acids, anhydrides of alkanephosphonic acids, molecular sieves or urea derivatives. 1,1'-Carbonyldiimidazoles and alkanephosphonic anhydrides are preferred, while alkanephosphonic anhydrides are particularly preferred.

In a preferred embodiment 1,1'-carbonyldiimidazole is suspended in THF and heated. 2-[4-(1,2,4-Oxadiazol-5-on-3-yl)-phenylamino]-acetic acid is added. The correspondingly substituted diaminobenzene is added to THF. The reaction mixture is stirred at about 50° C. and subsequently, after the addition of acetic acid, evaporated down and mixed with water and the solid substance is filtered off, washed and dried.

In a second particularly preferred embodiment, alkanephosphonic anhydrides are added, in the presence of an organic base, preferably a tert. amine such as e.g. DIPEA, to a solution of 2-[4-(1,2,4-oxadiazol-5-on-3-yl)-phenylamino]-acetic acid and correspondingly substituted diaminobenzene in THF. The reaction mixture is stirred, preferably at temperatures between −10 and 50° C., and subsequently, after the addition of acetic acid, evaporated down. It is combined with ethanol/water and optionally a filter aid, for example kieselguhr (e.g. Clarcel®), and filtered hot. Then the substance precipitated from the cooled solution is filtered off, washed and dried.

(B) The hydrogenation of step (b)i) is carried out in the presence of an inert diluent and a hydrogenation catalyst.

Particularly preferred is a process in which the hydrogenation is carried out in a temperature range from 0° C. to 100° C., preferably from 0° C. to 70° C., particularly from 25° C. to 60° C.

Also preferred is a process wherein the hydrogenation is carried out under a pressure of more than 0.5 bar to 100 bar, preferably under a pressure of 1 bar to 10 bar, particularly at about 1-5 bar.

The inert diluents may be both protic solvents—such as e.g. alcohols, carboxylic acids and/or water, or aprotic polar solvents such as e.g. ethers and/or amides or lactams and/or mixtures thereof. Water may optionally be added to all the solvents. The protic solvents used are preferably branched or unbranched $C_1$-$C_8$ alkanols, $C_1$-$C_3$ carboxylic acids or mixtures thereof Particularly preferably, lower alcohols such as methanol, ethanol, n-propanol and isopropanol, carboxylic acids such as formic acid, acetic acid and propionic acid or mixtures thereof are used. It is particularly preferable to use as the reaction medium ethanol and/or acetic acid, which may optionally contain water. Suitable aprotic solvents include polar ethers such as for example tetrahydrofuran, dioxane or dimethoxyethylether or amides such as for example dimethylformamide, or lactams such as for example N-methylpyrrolidone. Particularly preferred are THF and/or acetic acid, which may optionally contain water in any proportion. Preferably, solvents with a low tendency to flammability are used. Aprotic solvents are preferable to protic solvents during the hydrogenation.

Suitable hydrogenation catalysts are generally transition metals such as for example nickel, platinum or palladium or the salts or oxides thereof Raney nickel, platinum oxide and palladium on an inert carrier material, particularly palladium on activated charcoal (Pd/C) are preferred.

Processes in which the product of step (a) is used in a ratio by weight to the hydrogenation catalyst of 1:1 to 1000:1, preferably from 5:1 to 100:1 during hydrogenation are preferred.

In a preferred embodiment of step (b)i) the product of step (a) is taken up in THF/water (7:3 based on the volume) and hydrogenated at 4 bar hydrogen with water-moistened 10% Pd/C at about 40° C. The catalyst is filtered off, the filter is washed with THF/water (7:3) and the filtrate is clarified with active charcoal. The charcoal is filtered off and the filter is washed with THF and water. The filtrate thus obtained is reacted further directly in step b)ii).

(C) The optional subsequent carbonylation in step (b)ii), in order to obtain from a compound of formula (I), wherein $R^3$ denotes hydrogen, a compound of formula (I) wherein $R^3$ has a meaning other than hydrogen, without intermediate isolation of the hydrogenation product, is carried out by direct reaction of the compound of formula (I) obtained in step (b)i), wherein $R^3$ denotes hydrogen, with a carbonylation agent $R^3$—X, where $R^3$ has the meanings given above with the exception of hydrogen and X denotes a leaving group. Preferably X may denote a halogen such as for example chlorine or bromine or a p-toluenesulphonyl, methanesulphonyl or trifluoromethanesulphonyl group. Most particularly preferred is n-hexylchloroformate for preparing a compound of formula (I), wherein $R^3$ denotes n-hexyl. The reaction is preferably carried out at a temperature of 0 to 50° C., in particular at 10 to 20° C. in the presence of a base. The base used may conveniently be an alkali metal carbonate such as for example potassium carbonate or sodium carbonate, an alkali metal hydrogen carbonate such as for example sodium hydrogen carbonate or potassium hydrogen carbonate or a tertiary amine such as for example triethylamine. Preferably potassium carbonate is used. The reaction may for example be carried out in mixtures of water and acetone, water and dioxane or water and THF; a water/THF mixture is preferred.

After the reaction has ended a clear two-phase mixture may be formed by heating the suspension, e.g. to approx. 50° C., so that the aqueous phase, which contains a large proportion of the inorganic constituents, can be separated off. Then a change of solvent may take place. Suitable solvents include for example ketones or esters such as MIBK, butyl acetate, ethyl acetate, propyl acetate, isopropyl acetate or isobutyl acetate. Preferably MIBK or butyl acetate are used; butyl acetate is particularly preferred.

In a preferred embodiment of step (b)ii) the product of step (b)i) (=the filtrate from the hydrogenation) is combined at ambient temperature with an aqueous potassium carbonate solution. Then the carbonylation agent, for example n-hexyl chloroformate, is metered in at a temperature of 10-20° C. The suspension is heated to 50° C. during which time a clear two-phase mixture is formed. Depending on the results of the conversion check carried out further carbonylation agent is optionally metered in at approx. 50° C. until the reaction of the educt is complete. Then the THF is distilled off and replaced by butyl acetate. The organic phase is repeatedly washed with water with heating to 50-70° C., in order to eliminate polar impurities. Any residual moisture remaining is subsequently removed by azeotropic distillation.

D) Then before the precipitation of the salt in step (b)iii) a change of solvent may take place. For this, the organic solvent used previously, such as butyl acetate, is distilled off and replaced by the solvent for the salt precipitation. Suitable solvents for the partial step (b)iii) include for example ketones such as for example acetone or MIBK, ethers such as for example THF, esters such as for example ethyl acetate, isopropyl acetate or butyl acetate or alcohols such as for example methanol, ethanol or isopropanol. Preferably acetone and/or ethanol are used, particularly preferably a mixture of the two solvents is used. Then, by the addition of the corresponding acid, for example methanesulphonic acid for preparing the methanesulphonate, expediently 1 equivalent thereof, the desired salt may be precipitated and isolated directly.

In a preferred embodiment of step (b)iii), after a change of solvent to a mixture of acetone and ethanol, at a temperature of approx. 30-36° C. a solution of the corresponding acid, e.g. methanesulphonic acid, in acetone is slowly added to the product of step (b)ii) (=carbonylation solution) in the presence of seed crystals. The suspension is stirred, and the precipitated product is isolated by filtration, washed with acetone and dried under suitable conditions.

(E) In order to prepare 2-[4-(1,2,4-oxadiazol-5-on-3-yl)-phenylamino]-acetic acid, 2-[4-(1,2,4-oxadiazol-5-on-3-yl)-aniline is reacted with a 2-haloacetic acid ester, preferably ethyl bromoacetate, in the presence of a weak base, preferably a tertiary amine, such as for example triethylamine or an alkali metal carbonate, such as for example sodium carbonate in an inert solvent, and the 2-[4-(1,2,4-oxadiazol-5-on-3-yl)-phenylamino]-acetic acid ester obtained is saponified.

The inert diluents used may be both protic solvents—such as e.g. alcohols, and/or water—or aprotic polar solvents such as e.g. ethers and/or amides or lactams and/or mixtures thereof Water may optionally be added to all the solvents. Protic solvents used are preferably water or branched or unbranched $C_1$-$C_8$ alkanols or mixtures thereof Particularly preferably, water or lower alcohols such as methanol, ethanol, n-propanol and isopropanol or mixtures thereof are used. Most particularly preferably, ethanol is used as reaction medium, and this may optionally contain water. Isopropanol, optionally together with water, may also be used. The most suitable solvent is water, however. Suitable aprotic solvents are polar ethers such as for example tetrahydrofuran or dimethoxy-ethylether or amides such as for example dimethylformamide, or lactams such as for example N-methylpyrrolidone.

In a particularly preferred embodiment ethyl bromoacetate is metered into a suspension of 2-[4-(1,2,4-oxadiazol-5-on-3-yl)-aniline and sodium carbonate in water/isopropanol or preferably in water/ethanol and stirred at 35-45° C. The cooled suspension is suction filtered, washed with water and ethanol in several batches and dried.

The saponification is preferably carried out in a protic solvent with an alkali metal or alkaline earth metal hydroxide, particularly with lithium, sodium or potassium hydroxide.

In a particularly preferred embodiment 2-[4-(1,2,4-oxadiazol-5-on-3-yl)-phenylamino]-acetic acid ester is suspended in water or preferably in water/ethanol and slowly combined with an aqueous solution of NaOH at ambient temperature. The suspension changes into a solution and is heated to 45 to 75° C. HCl is added to the solution thus obtained until a pH of about 5 or preferably pH 3 is achieved. The solid is isolated and washed with cold water and cold ethanol and MtBE.

(F) In order to prepare 2-[4-(1,2,4-oxadiazol-5-on-3-yl)-aniline, 4-aminophenyl-amidoxime is reacted with a dialkyl carbonate, preferably dimethyl carbonate or diethyl carbonate in the presence of a base, preferably an alkali metal alkoxide, particularly sodium methoxide, sodium ethoxide or potassium tert-butoxide.

4-aminophenyl-amidoxime may be prepared e.g. by reacting 4-aminobenzonitrile with hydroxylamine hydrochloride.

In a particularly preferred embodiment sodium methoxide or preferably sodium ethoxide is added at 65-75° C., preferably at 70-75° C., to a suspension of 4-aminophenyl-amidoxime in ethanol and rinsed with ethanol. After 15 min stirring diethyl carbonate or preferably dimethyl carbonate is added dropwise. After 2-4 hours reaction time the mixture is cooled and ethanol is distilled off at 120 mbar and 40° C. The residue is taken up in water and after heating adjusted to pH 10-12 using semi-conc. sodium hydroxide solution, then to pH<6, preferably to pH<4, particularly preferably to pH 2-3, by acidifying with conc. hydrochloric acid, and slowly cooled. The solution changes into a suspension, which is filtered and washed several times with cold water and ethanol.

The preparation of the 2-[4-(1,2,4-oxadiazol-5-on-3-yl)-phenylamino]-acetic acid needed as intermediate product from 4-aminobenzonitrile is illustrated in the following reaction plan:

Diagram I
(The non-isolated intermediate stages indicated by square brackets may optionally vary between the different process variants. A preferred embodiment is shown.)

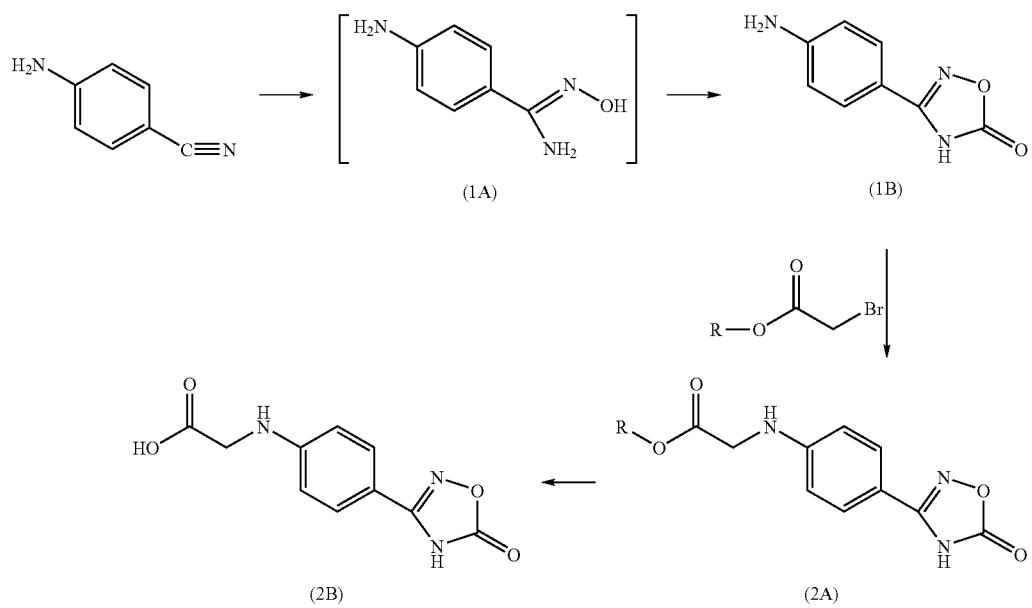

The preparation of a 4-(benzimidazol-2-ylmethylamino)-benzamidine is shown by way of example in the following reaction plan:
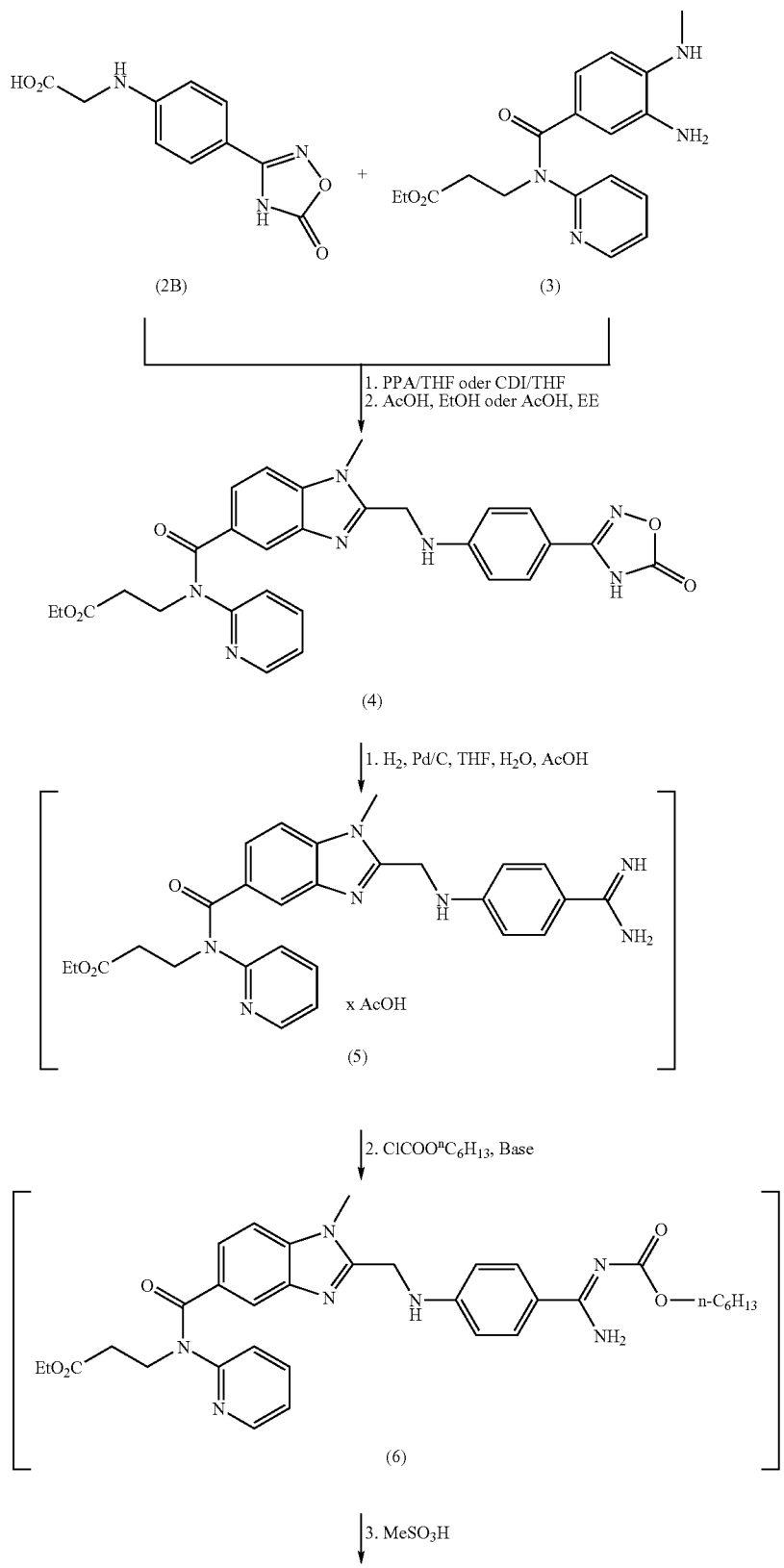

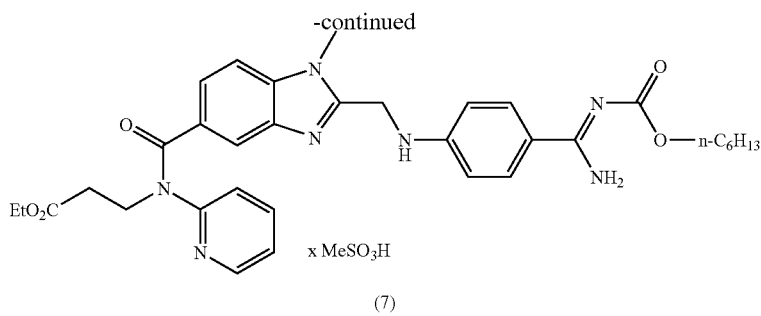

x MeSO₃H (7)

The working up of the individual reactions may take place in the conventional manner, for example, by separating off the reaction adjuvants, eliminating the solvent and isolating pure end product from the residue by crystallisation, distillation, extraction or chromatography.

In the last step of the process described above the compound of formula (I) thus obtained is converted into a physiologically acceptable salt. The physiologically acceptable salts may be salts with inorganic or organic acids or, if the compound contains a carboxy group, with inorganic or organic bases. Examples of acids for this purpose include methanesulphonic acid, hydrochloric acid, hydrobromic acid, sulphuric acid, phosphoric acid, fumaric acid, succinic acid, lactic acid, citric acid, tartaric acid or maleic acid. Examples of bases which may be used include sodium hydroxide, potassium hydroxide, cyclohexylamine, ethanolamine, diethanolamine and triethanolamine. The compound of formula (6) is preferably converted into its mesylate.

The process according to the invention will now be illustrated by means of the following Examples. The skilled man is aware that the Examples serve only as an illustration and are not to be regarded as restrictive.

EXAMPLES

The following abbreviations are used hereinbefore and hereinafter:

| | |
|---|---|
| AcOH | acetic acid |
| AMBPA | 3-amino-4-methylaminobenzoic acid-N-(2-pyridyl)-N-(2-ethoxycarbonylethyl)-amide |
| CDI | 1,1'-carbonyldiimidazole |
| DIPEA | diisopropylethylamine |
| EE | ethyl acetate |
| EtOH | ethanol |
| HCl | hydrochloric acid |
| MIBK | methylisobutylketone (4-methyl-2-pentanone) |
| MtBE | methyl-tert-butylether |
| NaOH | sodium hydroxide |
| NMP | N-methylpyrrolidone |
| PPA | propanephosphonic anhydride |
| PTSA | p-toluenesulphonic acid |
| RT | ambient temperature |
| THF | tetrahydrofuran |
| decomp. | decomposition |

Example 1

Preparation of 2-[4-(1,2,4-oxadiazol-5-on-3-yl)-aniline (1B)

(1A)

In the reaction vessel are placed 41.3 g (0.35 mol) 4-aminobenzonitrile and 36.5 g (0.53 mol) hydroxylamine-hydrochloride in 175 ml of ethanol and the mixture is heated to 60° C. 170.1 g (0.53 mol) sodium ethoxide solution (~21% in ethanol) are slowly added dropwise to this suspension.

The mixture is subsequently stirred overnight at 60° C. During cooling to 0-5° C. the substance is precipitated, filtered off and washed several times with a total of 70 ml cold ethanol. Approx. 86 g moist product are obtained. This is further processed directly.

(1B)

32 g (0.35 mol) dimethyl carbonate are added to a suspension of 86 g (1A) in 270 ml of ethanol. At 65-75° C., 125 g (0.38 mol) sodium ethoxide solution (~21% in ethanol) are added and rinsed with 20 ml of ethanol.

After 3 hours' reaction the mixture is cooled to 40° C. and the ethanol is distilled off at 120 mbar and 40° C. A dark residue is obtained. This is dissolved at 40-45° C. in 280 ml of water and after heating to 70° C. adjusted first to pH 11 by the slow addition of semi-conc. sodium hydroxide solution; then to pH 3-4 or preferably to pH 2-3 by acidifying with conc. hydrochloric acid and slowly cooled. The solution goes into a suspension, which is filtered and washed several times with a total of 50 ml cold water and 20 ml of ethanol. Approx. 88 g moist substance are obtained, which is dried at max. 50° C. in vacuo.

Yield: 48 g beige substance (77.5% of theory); melting point: from 178° C. (decomp.); purity: >98% HPLC peak area Example 2

Preparation of 2-[4-(1,2,4-oxadiazol-5-on-3-yl)-phenylamino]-acetic acid (2B)

(2A)

At 45° C. 60.2 g (0.36 mol) ethyl bromoacetate are metered into a suspension of 53.2 g (0.3 mol) (1B) and 19.1 g (0.18 mol) sodium carbonate in 500 ml of water/ethanol (90:10 to 95:5) and optionally stirred overnight. The reaction mixture is reddish-brown to orange. The suspension cooled to 0° C. is suction filtered, washed in several batches with 100 ml of ethanol and dried at max. 50° C. in vacuo.

Yield: 69.5 g brownish-beige substance (87.7% of theory); melting point: from 186.1° C. (decomp.); purity: >98% HPLC peak area (2B)

The ester (2A) (86.9 g; 0.33 mol) thus obtained is suspended in 400 ml of water or preferably ethanol/water (1:1) and at RT 120 g of 45% NaOH are slowly added dropwise. The suspension goes into solution and is reddish (pH 12.5). It is heated to ~60° C. and saponified for 1 h. The solution obtained is combined batchwise with HCl (37% or preferably with conc. HCl), until a pH 3 is obtained. It is cooled to 0° C. The solid is suction filtered and washed in several batches with a total of 400 ml cold water as well as 40 ml cold ethanol. 81.4 g moist substance are obtained. It is dried at 35° C. in vacuo.

Yield: 76.7 g substance (98% of theory)
melting point: from 193° C. (decomp.)
purity: >99% HPLC peak area

Example 3

Preparation of 3-amino-4-methylaminobenzoic acid-N-(2-pyridyl)-N-(2-ethoxycarbonylethyl)-amide (AMBPA) (3)

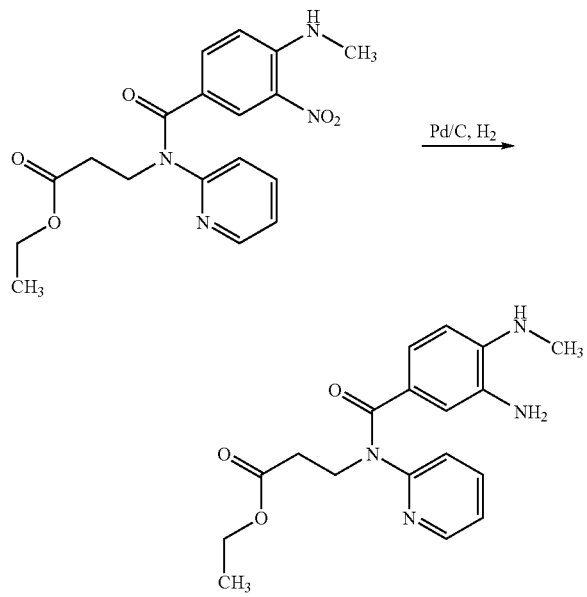

Variant A: Pd/C 5%

150 g (0.4 mol) 4-methylamino-3-nitrobenzoic acid-N-(2-pyridyl)-N-(2-ethoxycarbonylethyl)-amide, 12 g 5% palladium on charcoal catalyst and 627 ml of ethyl acetate are placed in a hydrogenating autoclave. The mixture is hydrogenated under a hydrogen atmosphere of 3-4 bar at 35-55° C. until the hydrogen uptake is constant (1-2 h). After cooling to 20° C. the hydrogenating solution is filtered off from the catalyst and evaporated down in vacuo using the rotary evaporator. The residue is taken up in 650 ml isopropanol, distilled down to half the original volume and cooled to 5-10° C. After 4 h the resulting suspension is filtered, and the precipitate thus isolated is washed batchwise with a total of 100 ml isopropanol. The solid obtained is dried in the vacuum dryer at 50° C.

Yield: 114.2 g (corr. 83% of theory)

Variant B: Pd/C 10%

25 g (0.07 mol) 4-methylamino-3-nitrobenzoic acid-N-(2-pyridyl)-N-(2-ethoxycarbonylethyl)-amide, 2.5 g 10% palladium on charcoal catalyst and 83 ml of ethyl acetate are placed in a hydrogenating autoclave. The mixture is hydrogenated under a hydrogen atmosphere of 3-4 bar at 50° C. until the hydrogen uptake is constant (4-5 h). After cooling to 20° C. the hydrogenating solution is filtered off from the catalyst and evaporated down in vacuo using the rotary evaporator. The residue is dissolved warm in a little ethyl acetate and combined with 68 ml of toluene. After cooling to 5° C. the mixture is left for 1 h with stirring, then the precipitate is filtered off and washed with toluene. The product obtained is dried at 40° C. in the vacuum dryer.

Yield: 20.9 g (corr. 91% of theory)

Example 4

Preparation of 1-methyl-2-[N-[4-(1,2,4-oxadiazol-5-on-3-yl)phenyl]-amino-methyl]-benzimidazol-5-yl-carboxylic acid-N-(2-pyridyl)-N-(2-ethoxycarbonyl-ethyl)-amide (4)

Variant A: CDI as Coupling Reagent 11.35 g (70 mmol) 1,1'-carbonyldiimidazole are suspended in 100 ml THF and heated to 50° C. 14.23 g (60.5 mmol) (2B) are added batchwise. 17.1 g (50 mmol) AMPBA 3 are dissolved in 37 ml THF with heating to 50° C.

After approx. 90 min the suspension is metered into the solution of AMPBA and rinsed with 20 ml THF.

The reaction mixture is stirred for approx. 18 h and subsequently, after the addition of 100 ml acetic acid, refluxed, so that the THF is distilled off. After approx. 1 h the mixture is combined with 400 ml of water and stirred.

The solution is cooled, the pink solid substance precipitated is filtered off and washed with 20 ml of water in 2 batches and dried at a maximum of 50° C. in vacuo.

Yield: 24.8 g substance (75% of theory); melting point: from 167° C. with decomp. (DSC); purity: >95% HPLC peak area Variant B: PPA as Coupling Reagent 34.2 g (0.1 mol) AMBPA 3, 27.5 g (0.12 mol) (2B) and 30.3 g (0.23 mol) DIPEA are placed in 170 ml THF and cooled to somewhat below ambient temperature. Now 85 g (0.13 mol) PPA (as ~50% solution in ethyl acetate) are metered in. The mixture is stirred for another 90 min and then the solvent is distilled off. Towards the end 73.5 g acetic acid are added and the mixture is heated to an internal temperature of 90° C. Then 400 ml of ethanol or preferably 400 ml of ethanol/water (approx. 85:15) and kieselguhr filtering adjuvant (e.g. Clarcel®) are added and the mixture is filtered hot. The solution is cooled, the solid substance precipitated is filtered off and washed in 2 batches with 50 ml of ethanol and dried at max. 50° C. in vacuo.

Yield: 56 g substance (85% of theory); melting point: from 167° C. with decomp. (DSC); purity: >95% HPLC peak area Variant C: Pivaloyl Chloride as Coupling Reagent 96 g (0.41 mol) (2B) are suspended in 250 ml NMP and 550 ml THF at 0° C. The thin suspension is combined successively with 48 g (0.4 mol) pivaloyl chloride and 52 g (0.4 mol) DIPEA and stirred for 30 minutes. Then 125 g (0.36 mol) AMBPA 3 dissolved in 800 ml acetic acid are added and the reaction mixture is refluxed for 3 h. THF is distilled off under a gentle vacuum and 1600 ml of water are metered in with heating. The solid is isolated at 5° C., washed with 550 ml of water and dried overnight in the circulating air dryer at max. 50° C.

Yield: 183 g (76%)
purity: >95% HPLC peak area

Example 5

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide (6) from 1-methyl-2-[N-[4-(1,2,4-oxadiazol-5-on-3-yl)phenyl]-amino-methyl]-benzimidazol-5-yl-carboxylic acid-N-(2-pyridyl)-N-(2-ethoxycarbonylethyl)-amide (4)

60 g (91 mmol) 1-methyl-2-[N-[4-(1,2,4-oxadiazol-5-on-3-yl)phenyl]-amino-methyl]-benzimidazol-5-yl-carboxylic acid-N-(2-pyridyl)-N-(2-ethoxycarbonylethyl)-amide (4) are hydrogenated with 3.0 g 10% palladium on charcoal (moistened with water) in 126 ml THF and 54 ml of water at 40° C. under 4 bar excess hydrogen pressure for 25 min. The hydrogenation solution is filtered and the filter is washed with 75 g THF/water (7:3). The filtrate is combined successively with 56 ml THF, 260 ml of water and batchwise with 75.2 g (544 mmol) potassium carbonate at ambient temperature. Then 14.2 g (86 mmol) of n-hexylchloroformate are metered in over 40 min. After the conversion level has been checked a further 1.2 g (7.3 mmol) n-hexylchloroformate are metered in, so that all the starting material is reacted. The suspension is heated to approx. 45° C. A clear two-phase mixture is formed. The aqueous phase is discarded and the THF is largely distilled off. 150 ml acetone are added to the suspension, it is heated to 50° C. and filtered clear. The filter is rinsed with 100 ml acetone. The filtrate is cooled to ambient temperature and the product is precipitated by the slow addition of 100 ml of water. The moist product is washed with 150 ml acetone/water (1:1) and 150 ml of water and dried in vacuo.

Yield: 56.9 g (94%)
HPLC-purity: >98.8%

Example 6

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide mesylate (7)

100 g (0.16 mol) of the compound (6) are dissolved in 890 ml acetone with heating and combined with a solution of 15 g (0.16 mol) methanesulphonic acid in 200 ml acetone. The solution is filtered and after the addition of 77 ml acetone cooled to approx. 20° C. The precipitated product is isolated and washed with acetone.

Then the mixture is dried at max. 50° C. in the vacuum dryer.

Yield: 90-98% (103-113 g)

Example 7

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide mesylate (7) from 1-methyl-2-[N-[4-(1,2,4-oxadiazol-5-on-3-yl)phenyl]-aminomethyl]-benzimidazol-5-yl-carboxylic acid-N-(2-pyridyl)-N-(2-ethoxycarbonylethyl)-amide (4)

60 g (91 mmol) of 4 (optionally containing acetate) are hydrogenated with 3.0 g 10% palladium on charcoal (moistened with water) in 126 ml THF and 54 ml of water at 40° C. and 4 bar excess hydrogen pressure for 30 min. The hydrogenation solution is filtered, the filter is washed with 51 g THF/water (7:3) and the filtrate is carburised. The activated charcoal is filtered off and the filter is washed with 102 ml THF and 80 ml of water. The filtrate is combined at ambient temperature with a solution of 75.2 g (544 mmol) potassium carbonate in 80 ml of water and at 10-20° C. 14.6 g (88.9 mmol) n-hexylchloroformate are metered in over 1 h. The suspension is heated to approx. 50° C. A clear two-phase mixture is formed, into which a further 0.452 g (2.7 mmol) n-hexylchloroformate are metered in after the conversion has been checked, so that all the starting material is reacted. After separation of the aqueous phase, 180 ml THF are subsequently distilled off and replaced by 350 ml butyl acetate. The organic phase is extracted twice with 30 ml of water at 50-70° C., 210 ml butyl acetate are distilled off and replaced by 300 ml acetone and 60 ml of ethanol. The reaction solution is cooled to 30-36° C., mixed with seed crystals of 7 (which have been obtained for example from a previous reaction according to Example 5 or using the process described in Example 3 of WO 03/074056) and a previously prepared solution of 7.84 g (82 mmol) methanesulphonic acid in 50 ml acetone is added dropwise. The suspension is stirred, the product is isolated by filtration and washed with acetone. The isolated substance is dried at 45° C. in vacuo.

Yield: 56.2 g (86%)
purity: >99% HPLC peak area

The other compounds of formula (I) and the salts thereof may be prepared analogously to the foregoing Examples.

What is claimed is:
1. A process for preparing a salt of an optionally substituted 4-(benzimidazol-2-ylmethylamino)-benzamidine of formula (I) with organic or inorganic acids,

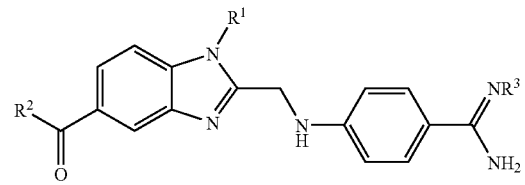

(I)

wherein
$R^1$ denotes a $C_{1-6}$-alkyl or $C_{3-7}$-cycloalkyl group,
$R^2$ denotes a $C_{1-6}$-alkyl group, a $C_{3-7}$-cycloalkyl group optionally substituted by a $C_{1-3}$-alkyl group, while the $C_{1-3}$-alkyl group may additionally be substituted by a carboxyl group, or
denotes an $R^{21}NR^{22}$ group, wherein
$R^{21}$ denotes a $C_{1-6}$ alkyl group which may be substituted by a carboxy, $C_{1-6}$ alkoxycarbonyl, benzyloxycarbonyl, $C_{1-3}$-alkylsulphonylaminocarbonyl, phenylsulphonylaminocarbonyl, trifluorosulphonylamino, trifluorosulphonylaminocarbonyl or 1H-tetrazolyl group,
a $C_{2-4}$-alkyl group substituted by a hydroxy, phenyl-$C_{1-3}$-alkoxy, carboxy -$C_{1-3}$-alkylamino, $C_{1-3}$-alkoxycarbonyl-$C_{1-3}$-alkylamino, N-($C_{1-3}$-alkyl)-carboxy -$C_{1-3}$-alkylamino or N-($C_{1-3}$-alkyl)-$C_{1-3}$-alkoxycarbonyl-$C_{1-3}$-alkylamino group, while in the above-mentioned groups the carbon atom in the α position to the adjacent nitrogen atom cannot be substituted, or
a piperidinyl group optionally substituted by a $C_{1-3}$-alkyl group, and
$R^{22}$ denotes a hydrogen atom, a $C_{1-6}$-alkyl group, a $C_{3-7}$-cycloalkyl group optionally substituted by a $C_{1-3}$-alkyl group, or a $C_{3-6}$-alkenyl or $C_{3-6}$-alkynyl group, while the unsaturated moiety may not be linked directly to the nitrogen atom of the $R^{21}NR^{22}$ group, a phenyl group optionally substituted by a fluorine, chlorine or bromine atom, by a $C_{1-3}$-alkyl or $C_{1-3}$-alkoxy group, or a benzyl, oxazolyl, isoxazolyl, thiazolyl, isothiazolyl, pyrazolyl, pyridinyl, pyrimidinyl, pyrazinyl, pyridazinyl, pyrrolyl, thienyl or imidazolyl group optionally substituted by a $C_{1-3}$-alkyl group, or
$R^{21}$ and $R^{22}$ together with the nitrogen atom between them denote a 5- to 7-membered cycloalkyleneimino group optionally substituted by a carboxy or $C_{1-4}$-alkoxycarbonyl group, to which additionally a phenyl ring may be fused, and $R^3$ denotes a $C_{1-9}$-alkoxycarbonyl, cyclohexyloxycarbonyl, phenyl -$C_{1-3}$-alkoxycarbonyl, benzoyl, p-$C_{1-3}$-alkyl-benzoyl or pyridinoyl group, while the ethoxy moiety in the 2 position of the above-mentioned $C_{1-9}$-alkoxycarbonyl group may additionally be substituted by a $C_{1-3}$-alkylsulphonyl or 2-($C_{1-3}$-alkoxy)-ethyl group, comprising the steps of:

(a) reacting phenyldiamine of formula (II)

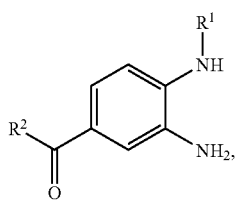
(II)

wherein $R^1$ and $R^2$ have the meanings given for formula (I), with 2-[4-(1,2,4-oxadiazol-5-on-3-yl)-phenylamino]-acetic acid to form a product of formula (III)

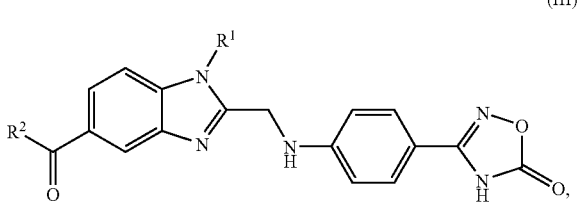
(III)

wherein $R^1$ and $R^2$ have the meanings given for formula (I), (b) i) hydrogenating the product of formula (III); and ii) reacting the product of step (b)(i), without any prior isolation, with a compound of formula (IV), $$R^3\text{---}X \quad \text{(IV)},$$

wherein $R^3$ of formula (IV) has the meaning given hereinbefore and X denotes a suitable leaving group; and iii) converting the product from step (b)(ii), without any prior isolation, into a physiologically acceptable salt.

2. Process according to claim 1 for preparing a salt of a compound of formula (I), wherein $R^1$ denotes a $C_{1-3}$-alkyl group, $R^2$ denotes an $R^{21}NR^{22}$ group, wherein $R^{21}$ denotes a $C_{1-3}$ alkyl group which may be substituted by a carboxy or a $C_{1-3}$ alkoxycarbonyl, and $R^{22}$ denotes a hydrogen atom, a $C_{1-3}$-alkyl group, a pyridinyl group optionally substituted by a $C_{1-3}$-alkyl group, and $R^3$ denotes a $C_{1-8}$-alkoxycarbonyl group.

3. Process according to claim 2 for preparing a salt of the compound of formula (I), wherein $R^1$ denotes a methyl group, $R^2$ denotes an $R^{21}NR^{22}$ group, wherein $R^{21}$ denotes an ethyl group which is substituted by an ethoxycarbonyl group, and $R^{22}$ denotes a pyridin-2-yl group, and $R^3$ denotes an n-hexyloxycarbonyl group.

4. Process according to claim 1, characterised in that the physiologically acceptable salt is the methanesulphonate, hydrochloride, maleate, tartrate, salicylate, citrate or malonate.

5. Process according to claim 4, characterised in that the physiologically acceptable salt is the methanesulphonate.

6. Process according to claim 1 characterised in that the condensation of step (a) is carried out in the presence of an inert diluent and a water-binding agent.

7. Process according to claim 1, characterised in that the hydrogenation of step (b)(i) is carried out in the presence of an inert diluent and a hydrogenation catalyst.

8. Process according to claim 1, characterised in that 2-[4-(1,2,4-oxadiazol-5-on-3-yl)-phenylamino]-acetic acid is prepared by reacting 4-(1,2,4-oxadiazol-5-on-3-yl)-aniline with a 2-haloacetic acid ester in the presence of a weak base, and the 2-[4-(1,2,4-oxadiazol-5-on-3-yl)-phenylamino]-acetic acid ester obtained is saponified.

9. Process according to claim 8, characterised in that 4-(1,2,4-oxadiazo-5-on-3-yl)-aniline is prepared by reacting 4-aminophenyl-amidoxime with a dialkyl carbonate in the presence of a base.

* * * * *